United States Patent [19]

Freidinger

[11] 4,152,322
[45] May 1, 1979

[54] PROCESS FOR SELECTIVE REDUCTION OF NITROARGINYL PEPTIDES WITH TITANIUM (III)

[75] Inventor: Roger M. Freidinger, Hatfield, Pa.

[73] Assignee: Merck & Co., Inc., Rahway, N.J.

[21] Appl. No.: 901,036

[22] Filed: Apr. 28, 1978

[51] Int. Cl.$^2$ ........................................... C07C 103/52
[52] U.S. Cl. ............................................. 260/112.5 R
[58] Field of Search ................................. 260/112.5 R

[56] References Cited

PUBLICATIONS

J. E. McMurry, Acc. Chem. Res. 7, 281 (1974).
J. E. McMurry et al., J. Org. Chem. 38, 4367 (1973).
J. E. McMurry, et al., J. Org. Chem. 40, 1502 (1975).
P. M. Scopes, et al., J. Chem. Soc. 782 (1965).
A. Turán, et al., Acta Chimica Academiae Scientiarum Hungaricae, 85, 327 (1975).
T. Hayakawa, et al., Bull. Chem. Soc. Jap., 40, 1205 (1967).
S. Sakakibara, et al., Bull. Chem. Soc. Jap., 41, 438 (1968).
M. Bodanzky et al., Peptides Synthesis, 2nd Edition, John Wiley & sons, N.Y., 67-68 (1976).

Primary Examiner—Delbert R. Phillips
Attorney, Agent, or Firm—Walter Patton; Harry E. Westlake, Jr.

[57] ABSTRACT

Nitroarginyl peptides are selectively reduced to the corresponding arginyl peptides by titanium (III). The nitro protecting group which is labile toward nucleophilic reagents is retained through part of a synthesis and selectively removed prior to treatment with nucleophiles such as hydrazine and ammonia. The selectivity of titanium (III) for removal of the nitro functionality increases the flexibility of this protecting group in the synthesis of arginyl peptides. The present novel process is useful in the synthesis of medicinal peptides such as molluscan cardiac stimulant H-Phe-Met-Arg-Phe-NH$_2$.

6 Claims, No Drawings

PROCESS FOR SELECTIVE REDUCTION OF NITROARGINYL PEPTIDES WITH TITANIUM (III)

BACKGROUND OF THE INVENTION

In the course of synthesis of biologically active arginine containing peptides, the guanidine group of arginine is protected with a nitro group. If it is desirable to treat the nitroarginine containing peptide with a nucleophilic reagent such as hydrazine or ammonia, it is necessary to selectively remove the nitro group because treatment of a nitroarginine peptide with a nucleophile such as ammonia would result in substantial or complete conversion of nitroarginine to ornithine.

In the prior art HF is used to remove the nitro protecting group from nitroarginine peptides. This process results in the complete or partial removal of other protecting groups such as the commonly used t-butyloxycarbonyl (Boc) group. According to the novel process of the present invention, the nitro group is selectively removed without loss of labile protecting groups such as the Boc protecting group.

The isonicotinyloxycarbonyl (i-NOC) group, a widely used protecting group for the ε-amino group of lysine, is removed by catalytic hydrogenation, electrolysis, and the two electron reducing agent zinc. These methods are also used in the prior art to remove the nitro group from nitroarginyl peptides, thus preventing the selective removal of the nitro group by these methods. According to the novel process of the present invention, the nitro group is selectively removed by treatment with titanium (III) in the presence of other labile protecting groups such as CBZ, Boc, Acm, benzyl, t-butyl and i-NOC.

The abbreviated designations, which are used herein for the amino acid components, certain preferred protecting groups, amino acid activation groups, condensing agents, reagents and solvents employed in the process of this invention are as follows:

| Abbreviated Designation | Amino Acid |
|---|---|
| Lys | L-lysine |
| Phe | L-phenylalanine |
| Trp | L-tryptophan |
| Cys | L-cysteine |
| Met | L-methionine |
| Arg | L-arginine |
| Gly | glycine |

| Abbreviated Designation | Protecting Groups |
|---|---|
| CBZ | benzyloxycarbonyl |
| Acm | acetamidomethyl |
| i-NOC | isonicotinyloxycarbonyl |
| Boc | tert-butyloxycarbonyl |
| OMe | methyl ester |

| Abbreviated Designation | Activating Groups |
|---|---|
| HBT | 1-hydroxybenzotriazole |

| Abbreviated Designation | Condensing Agents |
|---|---|
| DCCI | dicyclohexylcarbodiimide |

| Abbreviated Designation | Reagents |
|---|---|
| TFA | trifluoroacetic acid |
| TEA | triethylamine |

| Abbreviated Designation | Solvents |
|---|---|
| EPAW | ethyl acetate-pyridine-acetic acid-water |
| BAW | butanol-acetic acid-water |
| CMW | chloroform-methanol-water |
| DMF | dimethylformamide |
| THF | tetrahydrofuran |
| MeOH | methanol |
| HOAc | acetic acid |

SUMMARY OF THE INVENTION

According to the novel process of the present invention, the nitro group of nitroarginyl containing peptides is selectively removed by treatment with titanium (III) even in the presence of other labile protecting groups such as CBZ, Boc, Acm, benzyl, t-butyl and i-NOC.

A novel approach to the removal of the nitro protecting group from nitroarginine containing peptides is disclosed using the one electron reducing agent titanium trichloride. This reagent has been described before in J. E. McMurry, Acc. Chem. Res., 7, 281 (1974) but this reagent has not previously found application in peptide synthesis. The present process was investigated because titanium (III) has greater potential for selectivity than some of the reagents currently in use for removal of the nitro group such as those described in M. Bodansky et al., Peptide Synthesis, 2nd ed., John Wiley & Sons, New York, N.Y. 1976, p.67–68.

Several nitroarginine containing compounds were reduced under a variety of conditions to establish the effects of solvent, pH, and substitution at carboxyl and/or amino termini on product yield and by-product formation. These results are summarized in Table I.

TABLE I
Reduction of Nitroarginine Derivatives With TiCl$_3$

| Compound | Conditions | Arg | Orn | Unk. | % Yield |
|---|---|---|---|---|---|
| Boc-Arg(NO$_2$)-Gly-NH$_2$ | Buffered* aqueous MeOH | 97.6 | 2.4 | — | 83.6 |
| Boc-Arg(NO$_2$)-Gly-NH$_2$ | Aqueous MeOH,Et$_3$N | 71.4 | 28.6 | — | 62.4 |
| Boc-Arg(NO$_2$)-Gly-NH$_2$ | Buffered aqueous DMF | 78.0 | 21.2 | 0.8 | 73.4 |
| CF$_3$CO$_2$H . H-Arg(NO$_2$)-Gly-NH$_2$ | Buffered aqueous MeOH | 91.5 | 8.5 | — | 83.7 |
| CF$_3$CO$_2$H . H-Arg(NO$_2$)-Gly-NH$_2$ | 2N CF$_3$CO$_2$H | 90.8 | 6.6 | 2.6 | 77.5 |
| CF$_3$CO$_2$H . H-Arg(NO$_2$)-Gly-NH$_2$ | 2N HCl | 90.9$^b$ | 3.7 | 4.1 | 74.5 |
| CF$_3$CO$_2$H . H-Arg(NO$_2$)-Gly-NH$_2$ | Buffered H$_2$O | 80.7 | 17.6 | 1.9 | 71.8 |
| Boc-Arg(NO$_2$)-OH | Buffered aqueous MeOH | 91.2 | 8.8 | — | 92.6 |
| H-Arg(NO$_2$)-OH | 2N HCl | 91.5 | 4.4 | 4.1 | 72.0 |
| H-Arg(NO$_2$)-OH | 85% HOAc | 3.0 | 89.7 | 7.3 | 69.1 |
| H-Arg(NO$_2$)-OH | H$_2$O + 2.5 equiv. HOAc | 27.4 | 64.1 | 8.5 | 74.9 |

*Arginine Derived Products (%)[a]*

TABLE I-continued

| | Reduction of Nitroarginine Derivatives With TiCl₃ | | | | |
|---|---|---|---|---|---|
| | | Arginine Derived Products (%)[a] | | | |
| Compound | Conditions | Arg | Orn | Unk. | % Yield |
| Boc-Phe-Met-Arg(NO₂)-Phe-OCH₃ | Buffered aqueous MeOH | 99.0 | 1.0 | — | 77.0[c] |

*Buffered solutions are at pH 4 to 6
[a]Determined by amino acid analysis of total soluble reaction products. Less than quantitative recoveries were attributed to absorption losses on insoluble Ti(IV) species formed in the reactions.
[b]1.3% nitroarginine remained.
[c]Yield determined by isolation.

According to the process of the present invention, the nitroarginyl peptide is treated with titanium (III) at a pH range of 3 to 9, preferably at a pH of 3 to 7 maintained by a suitable buffer. The titanium (III) is conveniently used as an aqueous solution of titanium trichloride. A suitable solution is a 20% aqueous solution.

In the presence of extremely acid labile protecting groups, such as the Boc group, the reaction may be carried out in aqueous methanol solutions buffered at pH 4 to 6.

In most cases the reaction proceeds very rapidly, the reaction being over in about 5 min. to 1 hour. To insure complete reaction, 3 hours is sufficient. The temperature employed may be from 0° C. to 70° C. Of course, the higher the temperature, the shorter reaction time is necessary.

According to the process of the present invention, the nitroarginyl peptide is treated for 5 min. to 3 hours in dilute acid or aqueous methanol buffered at pH 3 to 7 with excess aqueous titanium (III) solution at a temperature range of 0° C. to 70° C. Yields of arginyl peptides were best and by-product formation least when the nitroarginyl compounds were treated for 1 hour in aqueous methanol containing ammonium acetate buffer (ph 4-6) with a slight excess of 20% aqueous titanium trichloride solution at 24° C. Similar conditions were employed by J. E. McMurry et al., *J. Org. Chem.* 38, 4364 (1973) but for the conversion of nitro to carbonyl. More acidic or basic conditions or other solvent combinations gave lower yields and more by-products. Compounds in which the nitroarginine residue has neither a free carboxyl nor a free amino terminus tended to react more cleanly. As with other methods for removal of the nitro group, formation of ornithine was the dominant side reaction and could not be entirely eliminated under any of the conditions tested.

The isonicotinyloxycarbonyl (i-Noc) group is a useful functionality for protection of the ε-amino group of lysine. It may be removed by catalytic hydrogenation, electrolysis, and the two electron reducing agent zinc. These procedures are also commonly applied to the removal of the nitro group from nitroarginyl peptides. α-Boc-ε-i-Noc-lysine showed no detectable reaction, according to tlc, after exposure to titanium trichloride for the usual period (1 hour), and only trace amounts of reaction were observed after 68 hours, thus according to the novel process of the present invention selective removal of the nitro group from nitroarginine in the presence of i-Noc-lysine is possible. Similarly, treatment of tryptophan with titanium (III) does not produce any detectable amount of by-product using the usual reaction conditions and only traces of by-products about 3 hours. Reduction of sulfoxides to sulfides with titanium trichloride has been reported by T. L. Ho et al., *Syn. thetic Commun.*, 3, 37 (1973). Using the conditions for nitro group removal, however, methionine sulfoxide was converted to methionine at a much slower rate than the nitro group cleavage. Methionine sulfone was inert to the reaction conditions.

These results demonstrate the selectivity of titanium (III) for removing the nitro group from nitroarginine derivatives. No other functionality commonly employed in peptide synthesis is significantly affected by the reagent titanium (III). In contrast, the usual conditions for removing the nitro group, including catalytic hydrogenation, anhydrous HF, zinc in acid, and electrolysis result in loss of one or more additional useful protecting groups.

Titanium (III) may be most valuable when the fragment condensation strategy is employed. Selective removal would be advantageous when nucleophilic reagents such as hydrazine or ammonia which react with the nitroguanidine are likely to be used. Such an application is illustrated by the synthesis of the molluscan cardiac stimulant Phe-Met-Arg-Phe-NH₂, designated compound (4) in Scheme 1 in which a key step involves removal of the nitro protecting group from arginine in tetrapeptide ester (1) with titanium (III) prior to ammonolysis. Compound (4) has been previously described in D. A. Price et al., *Science,* 197, 670 (1977). Treatment of compound (1) with ammonia would be expected to result in substantial if not complete, conversion of nitroarginine to ornithine.

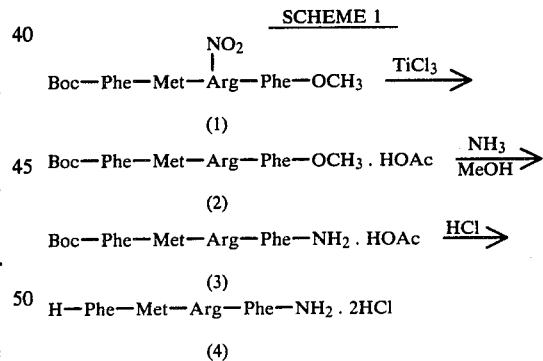

In a similar manner, fully protected nitroarginyl peptide fragments prepared using the solid phase could be selectively reduced to partially protected arginyl peptides with titanium (III) followed by conversion to the acyl hydrazides for subsequent coupling via the azide method.

The titanium (III) method for removing the nitro group from nitroarginyl peptides increases the utility and flexibility of this protecting group and permits useful strategies in fragment condensation syntheses which were not previously possible. Application of the nitro group for protecting arginine in combination with other protecting groups such as CBZ, Boc, Acm (cysteine), benzyl, t-butyl and i-Noc (lysine) which are also removable by chemically selective methods will make available formerly inaccessible partially protected peptides for biological evaluation. Titanium (III) will be a useful reagent whenever chemically selective removal of the nitro protecting group from nitroarginyl peptides is required.

The following Examples illustrate methods of carrying out the present invention, but it is to be understood that these Examples are given for purposes of illustration and not of limitation.

EXAMPLE 1

Preparation of Boc-Phe-Met-Arg(NO$_2$)-Phe-OCH$_3$(1)

Boc-Phe resin (3.42 g., 4.0 mmole of phenylalanine) was treated in a four cycle procedure according to the following scheme: (1) methylene chloride wash, 3×2 min.; (2) 1:1 (v/v) trifluoroacetic acid-methylene chloride deprotection (ethanedithiol added as a scavenger), 5 and 25 min.; (3) methylene chloride wash, 3×2 min.; (4) chloroform wash, 3×2 min.; (5) 1:9 (v/v) triethylamine-chloroform neutralization, 10 min.; (6) chloroform wash, 3×2 min.; (7) methylene chloride wash 3×2 min.; (8) Boc-amino acid (2.5 molar excess) in a minimum volume of methylene chloride followed after 5 min. by dicyclohexylcarbodiimide 2.5 molar excess in methylene chloride (1:1 v/v), 2 hours; (9) alternating methanol and methylene chloride washes, 3 each×2 min. All washes were 50 ml. Coupling efficiency was monitored with the Kaiser test set forth in *Anal. Biochem.*, 34, 595 (1970). The completed Boc-tetrapeptide was transesterified from the resin with triethylamine (7 ml.) in methanol (70 ml.) to provide 3.19 g. of crude product.

Amino acid analysis showed Phe 2.02, Arg 0.76, Met 0.64, Orn 0.22.

EXAMPLE 2

Preparation of Boc-Arg(NO$_2$)-Gly-NH$_2$

This process is adapted from R. L. Huguenin et al., *Helv. Chim. Acta*, 48, 1885 (1965). Boc-nitroarginine (7.12 g., 22.3 mmole), glycinamide hydrochloride (2.46 g., 22.3 mmole), triethylamine (3.0 ml., 22.3 mmole) and 1-hydroxybenzotriazole monohydrate (3.42 g., 22.3 mmole) were dissolved in a mixture of tetrahydrofuran (THF) (30 ml.), acetonitrile (30 ml.), and water (8 ml.). Dicyclohexylcarbodiimide (4.66 g., 22.6 mmole) in 10 ml. of 1:1 THF/acetonitrile was added dropwise during 10 min. The resulting mixture was stirred at room temperature for 17 hours, filtered, and the solid washed with 1:1 THF/acetonitrile. Most of the product was mixed with dicyclohexyl urea in the filtered solids. Crystallization from MeOH/ether gave pure Boc-Arg(NO$_2$)-Gly-NH$_2$, 5.95 g. (71% yield): mp 151°–153° C. (dec); $[\alpha]_{589}^{24}+0.21$, $[\alpha]_{463}^{24}+3.00$ (c, 1.4, MeOH).

Anal. Calcd. for C$_{13}$H$_{25}$N$_7$O$_6$: C, 41.60; H, 6.71; N, 26.12 Found: C, 41.48; H, 7.13; N, 26.31.

Amino acid analysis showed Arg 0.99, Gly 1.01.

EXAMPLE 3

General Procedure for Nitro Group Removal from Nitroarginyl Peptides with TiCl$_3$; Preparation of Boc-Phe-Met-Arg-Phe-OCH$_3$acetate (2)

A sample of compound (1), prepared according to the procedure described in Example 1, (1.52 g., 2 mmole) in 32 ml. of methanol under nitrogen was treated with a freshly prepared buffered solution of TiCl$_3$ consisting of 8 ml. (10.4 mmole) of 20% aqueous TiCl$_3$ and 18 ml. (72 mmole) of 4 M aqueous ammonium acetate. After 45 minutes, 3.5 ml. of dimethyl sulfoxide was added to oxidize excess TiCl$_3$. When the purple color was totally discharged (3.5 hours), the mixture was centrifuged at 5000 rpm. The supernatant was decanted and the solid titanium oxides were washed with methanol. The combined supernatants were concentrated in vacuo. Most remaining ammonium salts were precipitated by addition of isopropanol. Filtration and concentration in vacuo gave a crude product which was purified by preparative tlc on Quantum Q-1 silica gel plates (1000μ) using 15:5:1:2 ethyl acetate/pyridine/acetic acid/water as developing solvent. Elution of the major band with 1:1 methanol/methylene chloride gave 1.2 g. (77%) of Boc-Phe-Met-Arg-Phe-OCH$_3$acetate: mp 210° C. (dec); $[\alpha]_{589}^{24}-14.8$ (c, 0.40, methanol); ir (Nujol) 1740 cm$^{-1}$ (ester carbonyl).

Amino acid analysis showed Phe 2.18, Met 0.86, Arg 0.96.

EXAMPLE 4

Preparation of Boc-Phe-Met-Arg-Phe-NH$_2$acetate (3)

A solution of tetrapeptide ester (2) (1.0 g, 1.3 mmole) in 50 ml. of methanol in a pressure bottle was saturated at 0° C. with ammonia. The bottle was sealed and the solution was stirred at room temperature for 24 hours. Concentration of the solution in vacuo and precipitation of the residue from methanol/ether gave 710 mg. (73%) of amorphous Boc-Phe-Met-Arg-Phe-NH$_2$acetate: $[\alpha]_{589}^{24}-14.1$ (c, 1.0, methanol); ir (Nujol) 1645 cm$^{-1}$ (No ester carbonyl).

Amino acid analysis showed Phe 2.06, Met 0.94, Arg 1.00.

EXAMPLE 5

Preparation of H-Phe-Met-Arg-Phe-NH$_2$.2HCl (4)

Protected tetrapeptide amide (3) was deprotected with HCl/ethyl acetate. The crude product (330 mg., 79%) was purified by preparative tlc on Quantum Q-1 silica gel plates using 10:5:1:3 ethyl acetate/pyridine/acetic acid/water as both developing and eluting solvent. The eluted solution was concentrated in vacuo to a film, triturated with ethyl acetate to remove pyridinium acetate, and freeze dried from water to the hygroscopic solid H-Phe-Met-Arg-Phe-NH$_2$.2HCl (98 mg., 24%) $[\alpha]_{589}^{24}-4.4$ (c, 0.25, methanol).

Amino acid analysis showed Phe 2.00, Met 0.97, Arg 1.03.

EXAMPLE 6

Preparation of Boc-Arg-Gly-NH$_2$ acetate

Boc-Arg(NO$_2$)-Gly-NH$_2$, prepared by the process set forth in Example 2, (4.9 g., 13.1 mmole) was treated in methanol (195 ml.) according to the general procedure for removing nitro groups with a buffered solution of TiCl$_3$ made from 60 ml. (78 mmole) of 20% aqueous TiCl$_3$ and 117 ml. (468 mmole) of 4 M aqueous ammonium acetate. After oxidation of excess TiCl$_3$ by bubbling through air, work-up and silica gel column chromatography (10:5:1:3 ethyl acetate/pyridine/acetic acid/water) gave 4.0 g. (45%, corrected for peptide content) of Boc-Arg-Gly-NH$_2$ acetate: $[\alpha]_{589}^{24}-7.67$ (c, 2.92, 1 N acetic acid).

Amino acid analysis showed Arg 1.03, Gly 0.97, Orn 0.01.

What is claimed is:

1. A process for selectively cleaving the nitro group from nitroarginyl containing peptides with salts of titanium (III) at pH 3 to 9 in the presence of other labile protecting groups according to the reaction:

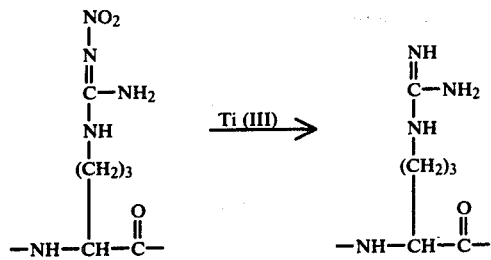

2. The process according to claim 1 for cleaving the nitro group from nitroarginyl containing peptides with titanium (III) trichloride in dilute acid or aqueous methanol buffered at pH 3 to 7.

3. The process according to claim 2 for cleaving the nitro group from nitroarginyl containing peptides with titanium (III) trichloride in dilute aqueous hydrochloric acid or aqueous methanol buffered at pH 4 to 6 in the presence of CBZ, Acm, benzyl, or i-NOC protecting groups.

4. The process according to claim 3 for cleaving the nitro group from nitroarginyl containing peptides with titanium (III) trichloride in aqueous methanol buffered at pH 4 to 6 in the presence of CBZ, Acm, Boc, benzyl, t-butyl or i-NOC protecting groups.

5. The process according to claim 4 for deprotecting nitroarginyl containing peptides by treating said peptides for 5 mins. to 3 hours in aqueous methanol containing ammonium acetate buffer at pH 4 to 6 with a slight excess of 20% aqueous titanium (III) trichloride solution at about 0° C. to 70° C.

6. The process according to claim 5 for deprotecting nitroarginyl containing peptides by treating said peptides for about 1 hour in aqueous methanol containing ammonium acetate buffer at pH 4 to 6 with a slight excess of about 20% aqueous titanium (III) trichloride solution at about 24° C.

* * * * *